(12) United States Patent
Kodama

(10) Patent No.: US 12,357,165 B2
(45) Date of Patent: Jul. 15, 2025

(54) ENDOSCOPE

(71) Applicant: Japan Lifeline Co., Ltd., Tokyo (JP)

(72) Inventor: Yuki Kodama, Tokyo (JP)

(73) Assignee: JAPAN LIFELINE CO., LTD., Tokyo (JP)

( * ) Notice: Subject to any disclaimer, the term of this patent is extended or adjusted under 35 U.S.C. 154(b) by 530 days.

(21) Appl. No.: 17/795,745

(22) PCT Filed: Mar. 23, 2020

(86) PCT No.: PCT/JP2020/012793
§ 371 (c)(1),
(2) Date: Jul. 27, 2022

(87) PCT Pub. No.: WO2021/191989
PCT Pub. Date: Sep. 30, 2021

(65) Prior Publication Data
US 2023/0096539 A1 Mar. 30, 2023

(51) Int. Cl.
*A61B 1/05* (2006.01)
*A61B 1/01* (2006.01)
*A61B 1/018* (2006.01)

(52) U.S. Cl.
CPC ............... *A61B 1/053* (2013.01); *A61B 1/01* (2013.01); *A61B 1/018* (2013.01)

(58) Field of Classification Search
CPC .......... A61B 1/01; A61B 1/018; A61B 1/053; A61B 1/0125; A61B 1/00135;
(Continued)

(56) References Cited

U.S. PATENT DOCUMENTS

| 6,585,639 B1* | 7/2003 | Kotmel | A61B 1/267 |
| | | | 600/116 |
| 2005/0272975 A1* | 12/2005 | McWeeney | A61B 1/307 |
| | | | 600/172 |

(Continued)

FOREIGN PATENT DOCUMENTS

| CN | 101461702 A | 6/2009 |
| CN | 204192562 U | 3/2015 |

(Continued)

OTHER PUBLICATIONS

Japanese Office Action issued for corresponding Japanese Patent Application No. 2022-509798 dated Sep. 17, 2024; pp. 1-8.
An Office Action in corresponding Vietnamese Application No. 1-2022-05048 dated Dec. 16, 2024.
Office Action of JP Application No. 2022-509798 dated May 16, 2023 and English translation, 6 pages.

(Continued)

*Primary Examiner* — Aaron B Fairchild
(74) *Attorney, Agent, or Firm* — MUNCY, GEISSLER, OLDS & LOWE, P.C.

(57) ABSTRACT

An object is to provide an endoscope by which it is possible to reuse a camera including an expensive solid-state image sensor. An endoscope of the present invention includes a shaft to be inserted into a body, a handle mounted on a proximal end side of the shaft and including a grip and operation knobs, and a camera including a cable tube and a camera head equipped with an image sensor. The camera is separable from the handle and the shaft. The shaft is formed with a camera channel in which the camera is arranged, the handle is provided with a camera channel port communicating with the camera channel, and the cable tube of the camera is attached to a camera connector mounted to the camera channel port when the camera is arranged in the camera channel.

10 Claims, 11 Drawing Sheets

(58) Field of Classification Search
CPC ............ A61B 1/00147; A61B 1/00154; A61B 1/0016; A61B 1/04; A61B 1/041; A61B 1/042; A61B 1/05
USPC .......................................................... 600/112
See application file for complete search history.

(56) References Cited

U.S. PATENT DOCUMENTS

| | | | |
|---|---|---|---|
| 2006/0149129 A1* | 7/2006 | Watts ................ | A61M 25/0152 600/113 |
| 2008/0086029 A1* | 4/2008 | Uchiyama ............ | A61B 1/0016 600/114 |
| 2010/0204546 A1 | 8/2010 | Hassidov et al. | |
| 2015/0057537 A1* | 2/2015 | Dillon ................. | A61B 1/0014 600/113 |
| 2016/0262601 A1 | 9/2016 | Viebach et al. | |

FOREIGN PATENT DOCUMENTS

| | | | | |
|---|---|---|---|---|
| CN | 206390875 | U | 8/2017 | |
| CN | 109846443 | A | 6/2019 | |
| DE | 102014110328 | A1 | 1/2015 | |
| JP | 2000210249 | A | 8/2000 | |
| JP | 2007530155 | A | 11/2007 | |
| JP | 4764417 | B2 | 9/2011 | |
| JP | 2016536062 | A | 11/2016 | |
| JP | 2019536547 | A | 12/2019 | |
| JP | 202062243 | A | 4/2020 | |
| WO | WO-2018095893 | A1 * | 5/2018 | ......... A61B 1/00135 |

OTHER PUBLICATIONS

An Office Action in corresponding JP Application No. 2022-509798 dated Jul. 25, 2023, 3 pages.

* cited by examiner

ENDOSCOPE

TECHNICAL FIELD

The present invention relates to an endoscope and more particularly relates to an endoscope including a shaft to be inserted into a body, a handle for operation, and a camera.

BACKGROUND ART

In the related art, an endoscope including a shaft to be inserted into a body, a handle for operation, and a camera is known as a small endoscope used in diagnosis and treatment of a bile duct, a pancreatic duct, and the like via a duodenum endoscope (see Patent Document 1 below).

The shaft constituting the endoscope is provided with a camera (including a transmission cable) and an optical fiber, and a water supply channel and a forceps channel are formed in the shaft.

A solid-state image sensor (CMOS image sensor) is mounted in the camera arranged in the shaft and constituting the endoscope.

CITATION LIST

Patent Literature

Patent Document 1: JP 4764417 B

SUMMARY OF INVENTION

Technical Problem

A small endoscope such as described in Patent Document 1 is equipped with a camera including an expensive solid-state image sensor. Therefore, it is desirable to reuse such an endoscope.

However, it is difficult to clean small endoscopes, and the camera may be damaged during cleaning. Thus, it is not feasible to reuse the small endoscope described in Patent Document 1, and the endoscope is discarded together with the camera after use.

The present invention has been made on the basis of these circumstances.

A first object of the present invention is to provide an endoscope by which it is possible to reuse a camera including an expensive solid-state image sensor.

A second object of the present invention is to provide an endoscope by which it is possible to prevent a shaft from being inserted into a delivery device or a body when a camera protrudes from a distal end surface of the shaft.

A third object of the present invention is to provide an endoscope by which it is possible to precisely adjust a distal end position of a camera relative to a distal end surface of the shaft.

Solution to Problem (1) An endoscope of the present invention includes a shaft to be inserted into a body,
- a handle mounted on a proximal end side of the shaft, and
- a camera including a cable tube and a camera head, the camera head being equipped with an image sensor,
- the camera being separable from the handle and the shaft.

According to an endoscope having such a configuration, after the endoscope is used, the camera can be separated from the handle and the shaft and cleaned, making it is possible to reuse the camera, which is an expensive component of the endoscope.

(2) It is preferable that the shaft is formed with a camera channel in which the camera is arranged,
- the handle is provided with a camera channel port communicating with the camera channel, and
- the cable tube of the camera is attached to a camera connector mounted to the camera channel port when the camera is appropriately arranged in the camera channel.

According to an endoscope having such a configuration, the camera can be appropriately arranged in the camera channel by inserting the camera from the camera channel port provided in the handle, inserting the camera into the camera channel formed on the shaft, and mounting, to the camera channel port, the camera connector attached to the cable tube of the camera.

(3) In the endoscope according to (2) described above, it is preferable that the camera connector includes a camera position adjustment mechanism configured to reciprocate the camera to displace the camera between a first position where, when the camera connector is mounted to the camera channel port, a distal end of the camera arranged in the camera channel is located on a proximal end side of a distal end surface of the shaft where the camera channel opens, and a second position where, when the camera connector is mounted to the camera channel port, the distal end of the camera is located on a distal end side of the distal end surface of the shaft.

According to an endoscope having such a configuration, a distal end position of the camera with respect to the distal end surface of the shaft can be precisely adjusted between the first position and the second position.

In addition, by positioning the distal end of the camera to the first position by using the camera position adjustment mechanism, and then, inserting the camera into the camera channel, it is possible to prevent the camera from being inserted into a delivery device or a body when the camera protrudes from a distal end surface of the shaft.

(4) In the endoscope according to (3) described above, a distance from the first position to the second position is preferably from 2 to 100 mm.

(5) In the endoscope according to (3) or (4) described above, the camera position adjustment mechanism is preferably a mechanism configured to reciprocate the camera by utilizing a feed screw.

(6) In the endoscope according to (5) described above, it is preferable that the camera position adjustment mechanism includes a connector case mounted to the camera channel port and having an inner peripheral surface formed with a guide groove extending along an axial direction,
- a slide member slidable with respect to the connector case and including a shaft part and a guide part, the shaft part extending inside the connector case and a part of the shaft part protruding to a proximal end side of the connector case, a male screw part being formed at least in a proximal end portion of the shaft part, and the cable tube of the camera being fixed to an inside of the shaft part in a state of being inserted through the shaft part, the guide part being integrally formed with the shaft part and surrounding a distal end portion of the shaft part, the guide part having an outer peripheral surface formed with a ridge part to be guided by the guide groove, and
- a rotation knob positioned on the proximal end side of the connector case, restricted from moving in the axial direction, and including a female screw part to be screwed into the male screw part of the shaft part of the slide member, and when the rotation knob is rotated in one direction, the camera position adjustment mechanism slides the slide member from the proximal end position to the distal end position to move the distal end of the camera from the first position to the second position, and when the rotation knob is rotated in an other direction, the camera position adjustment mechanism slides the slide member from the distal end position to the proximal end position to move the distal end of the camera from the second position to the first position.

(7) The endoscope according to (6) above preferably includes a connector mounting restriction mechanism configured to prevent the camera connector from being mounted to the camera channel port when the slide member of the camera position adjustment mechanism is not in the proximal end position.

According to an endoscope having such a configuration, when the slide member is not in the proximal end position, it is not possible to arrange the camera in the camera channel (mount the camera in the endoscope), and thus the shaft can be reliably prevented from being inserted into a delivery device or a body when the camera protrudes from the distal end surface of the shaft.

(8) In the endoscope according to (7) described above, it is preferable that the connector mounting restriction mechanism includes a port-side connector mounted to the camera channel port and interposed between the camera channel port and the camera connector, the port-side connector is formed with an insertion passage for the cable tube, when the slide member is in the proximal end position, a proximal end portion of the port-side connector is not prevented from being inserted into the connector case to couple the port-side connector and the camera connector, and when the slide member is not in the proximal end position and insertion of the proximal end portion of the port-side connector into the connector case is performed, the insertion of the proximal end portion of the port-side connector is prevented by interference between the proximal end portion of the port-side connector and a distal end of the slide member.

(9) In the endoscope according to (8) described above, it is preferable that a through hole having a circular shape is formed in a peripheral wall of the connector case, a distal end portion of the port-side connector is inserted into the handle from the camera channel port, the proximal end portion of the port-side connector includes an inner tube part forming an insertion passage of the shaft part of the slide member and an outer tube part having an outer peripheral shape formed in accordance with an inner peripheral shape of the connector case, a peripheral wall of the outer tube part is formed with notches configured to allow contact with the ridge part of the guide part to be avoided when the slide member slides, and a protrusion having a hemispherical shape is formed on an outer peripheral side of a peripheral wall portion sandwiched between the notches and having flexibility, when the slide member is in the proximal end position and insertion of the proximal end portion of the port-side connector into the connector case is performed, the peripheral wall portion bends to retract the protrusion inward to prevent the protrusion from hindering the insertion of the proximal end portion of the port-side connector, and upon completion of the insertion of the proximal end portion of the port-side connector into the connector case, the peripheral wall portion being bent returns to an original posture and the protrusion is fitted into the through hole of the connector case, and when the slide member is not in the proximal end position and insertion of the proximal end portion of the port-side connector into the connector case is performed, the insertion of the proximal end portion of the port-side connector is prevented by interference between the peripheral wall portion being inwardly bent and the distal end of the slide member.

(10) In the endoscope according to (3) or (4) described above, the camera position adjustment mechanism may include a fixed member mounted to the camera channel port and a movable member configured to move in the axial direction with respect to the fixed member, the cable tube of the camera being fixed to an inside of the movable member in a state of being inserted through the movable member, when the movable member in a proximal end position is pushed and moved to a distal end position, the camera position adjustment mechanism may move the distal end of the camera from the first position to the second position, when the movable member in the distal end position is retracted and moved to the proximal end position, the camera position adjustment mechanism may move the distal end of the camera from the second position to the first position, and the camera position adjustment mechanism may be a mechanism configured to provide a click feeling in response to a movement of the movable member.

(11) In the endoscope according to (10) described above, it is preferable that the camera position adjustment mechanism includes a click-producing indentation part formed in the movable member and a click-producing projection part provided in the fixed member and meshing with the click-producing indentation part.

(12) In the endoscope of the present invention, the camera is preferably equipped with an optical fiber.

(13) In the endoscope of the present invention, it is preferable that an outer diameter of the shaft is from 1.1 to 7.0 mm and a diameter of the camera channel is from 0.7 to 3.0 mm, and the shaft is formed with a forceps channel having a diameter from 0.3 to 3.0 mm.

According to the endoscope having such a configuration, it is possible to use general-purpose forceps while providing a shaft having a small diameter.

(14) The endoscope of the present invention can be suitably used for diagnosing and treating a disease in a bile duct or a pancreatic duct, a bronchial tube, or a bladder.

Advantageous Effects of Invention

According to an endoscope of the present invention, it is possible to reuse a camera including an expensive solid-state image sensor.

According to the endoscope of the present invention including a camera position adjustment mechanism, a distal end position of the camera with respect to a distal end surface of the shaft can be precisely adjusted between a first position and a second position.

In addition, by positioning the distal end of the camera to the first position by using the camera position adjustment mechanism, and then, inserting the camera into the camera channel, it is possible to prevent the camera from being inserted into a delivery device or a body when the camera protrudes from a distal end surface of the shaft.

DESCRIPTION OF EMBODIMENTS

First Embodiment

An endoscope 100 of the present embodiment illustrated in FIGS. 1 to 8 (FIGS. 8A and 8B) is used for diagnosing and treating a disease in a bile duct or a pancreatic duct.

The endoscope 100 includes a shaft 10 to be inserted into a body, a handle 20 mounted on a proximal end side of the shaft 10, and a camera 30.

Figure 1:
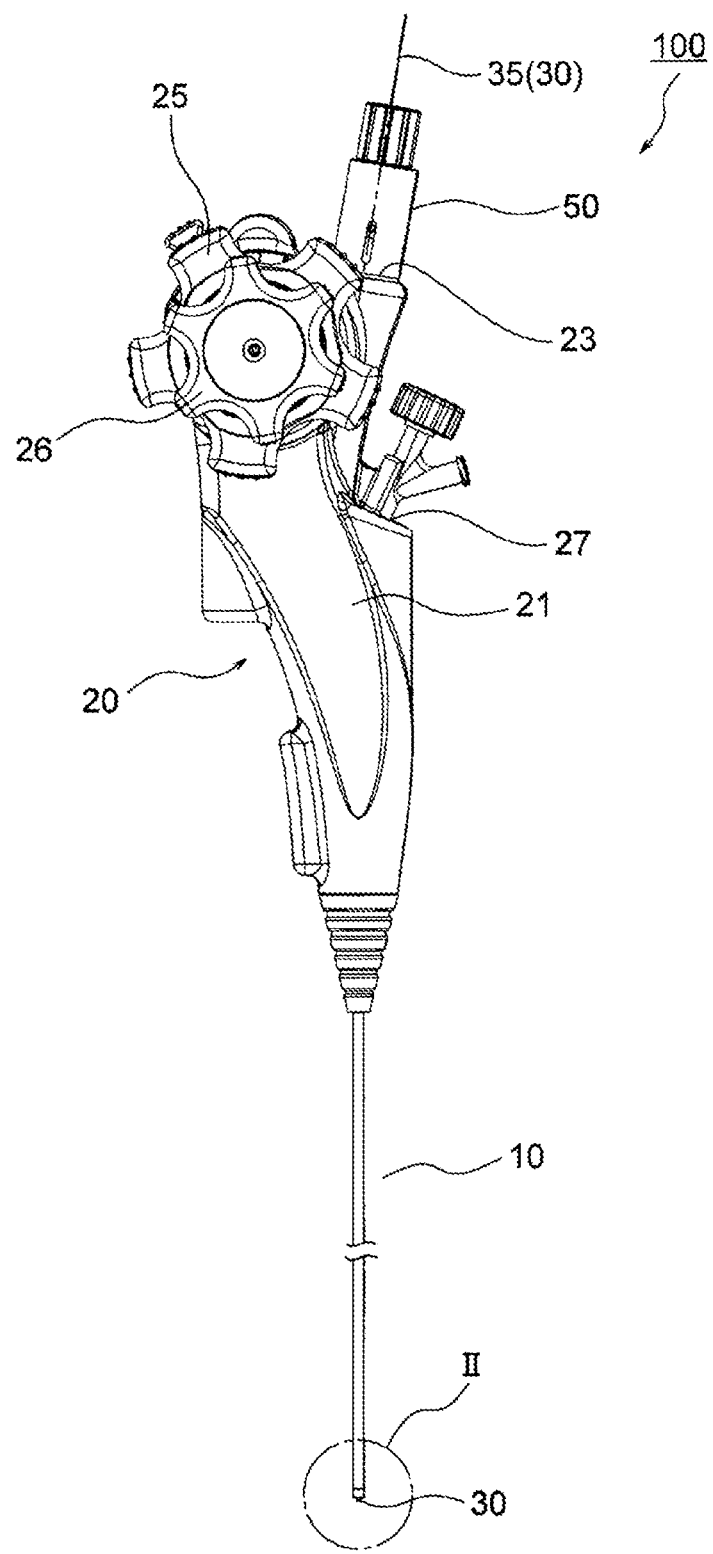
FIG. 1 is an explanatory diagram illustrating an outer appearance of a first embodiment of an endoscope of the present invention.
Figure 2:
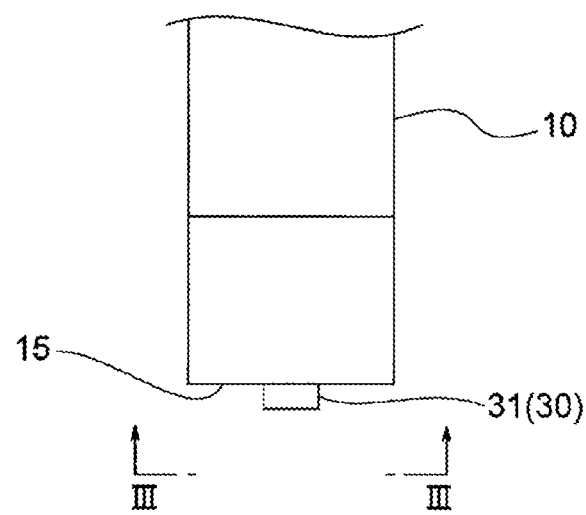
FIG. 2 is a partially enlarged view (detailed view of part II) illustrating a distal end part of the endoscope illustrated in FIG. 1.
Figure 3:
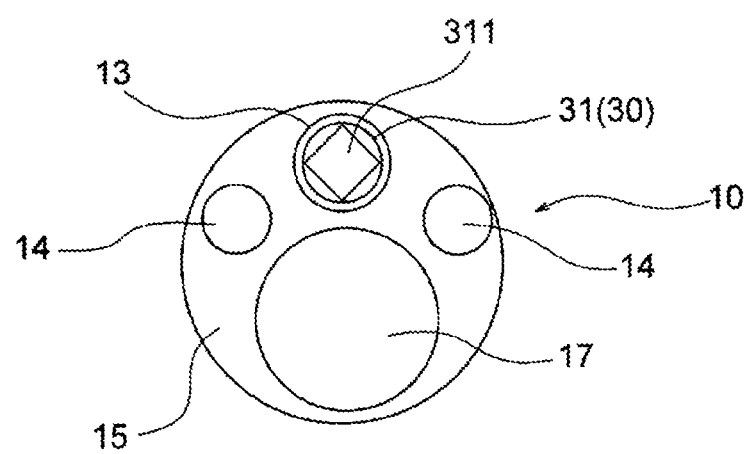
FIG. 3 is a diagram as viewed from a direction indicated by arrows III-III of FIG. 2.

As illustrated in FIG. 3, a camera channel 13, water supply channels 14, and a forceps channel 17 are formed in the shaft 10 constituting the endoscope 100.

An outer diameter of the shaft 10 is preferably from 1.1 to 7.0 mm, and a suitable example of the outer diameter is 3.6 mm.

A diameter of the camera channel 13 is preferably from 0.7 to 3.0 mm, and a suitable example of the diameter is 1.1 mm.

A diameter of the forceps channel 17 is preferably from 0.3 to 3.0 mm, and a suitable example of the diameter is 2.0 mm. When the diameter of the forceps channel 17 is 2.0 mm, it is possible to use general purpose forceps (diameter of 1.8 mm).

The handle 20 constituting the endoscope 100 includes a grip 21 and two operation knobs 25 and 26. The handle 20 is provided with a camera channel port 23 communicating with the camera channel 13 and a forceps channel port 27 communicating with the forceps channel 17.

The camera 30 constituting the endoscope 100 includes a camera head 31 equipped with a CMOS image sensor 311 and a cable tube 35 containing a transmission cable of the CMOS image sensor 311. An optical fiber (not illustrated) is incorporated into the camera 30 so as to surround the CMOS image sensor 311.

An outer diameter of the camera head 31 is preferably from 0.6 to 2.9 mm, and a suitable example of the outer diameter is 1.0 mm. An outer diameter of the cable tube 35 is substantially equal to the outer diameter of the camera head 31.

The camera 30 is arranged in the camera channel 13 of the shaft 10, a proximal end portion of the cable tube 35 protrudes to the outside from the camera channel port 23 of the handle 20, and a proximal end of the cable tube is connected to a control device.

The cable tube 35 of the camera 30 is attached to a camera connector 50.

The camera connector 50 is mounted to the camera channel port 23 of the handle 20 when the camera 30 is appropriately arranged in the camera channel 13 of the shaft 10.

That is, when the camera connector 50 is mounted to the camera channel port 23, the camera 30 is appropriately arranged in the camera channel 13.

An attachment position of the camera connector 50 is 300 to 3000 mm from a distal end of the camera 30, and a suitable example of the attachment position is 2100 mm from the distal end of the camera 30.

In the endoscope 100 of the present embodiment, the camera 30 is separable from the handle 20 and the shaft 10.

That is, the camera connector 50 can be removed from the camera channel port 23 to remove the camera 30 arranged in the camera channel 13 of the shaft 10 from the camera channel port 23 of the handle 20, together with the camera connector 50.

In addition, after being separated temporarily, the camera 30 can be inserted, with the camera head 31 first, from the camera channel port 23 of the handle 20 into an inner part of the handle 20 and the camera channel 13 of the shaft 10, and the camera connector 50 can be mounted to the camera channel port 23, making it possible to reincorporate the camera 30 as a constitution component of the endoscope 100.

The camera connector 50 includes a camera position adjustment mechanism that reciprocates the camera 30 with respect to the camera channel 13 so as to displace the camera 30 between a first position and a second position. The first position is a position where, when the camera connector 50 is mounted to the camera channel port 23, the distal end of the camera 30 arranged in the camera channel 13 is located on a proximal end side of a distal end surface 15 of the shaft 10 where the camera channel 13 opens (a distal end position of the camera 30 illustrated in FIG. 5A). The second position is a position where, when the camera connector 50 is mounted to the camera channel port 23, the distal end of the camera 30 is located on a distal end side of the distal end surface 15 (a distal end position of the camera 30 illustrated in FIG. 5B).

Here, a distance from the first position to the second position (a distance by which the distal end of the camera 30 is moved by the position adjustment mechanism) is preferably from 2 to 100 mm, and a suitable example of the distance is 30 mm.

Furthermore, a distance from the distal end surface 15 of the shaft 10 to the first position is preferably from 1.5 to 20 mm, and a distance from the distal end surface 15 to the second position is preferably from 0.5 to 80 mm.

In the endoscope 100 of the present embodiment, the camera position adjustment mechanism included in the camera connector 50 is a mechanism that utilizes a feed screw to reciprocate the camera 30.

Specifically, the camera position adjustment mechanism includes a connector case 51, a slide member 52, and a rotation knob 53. The connector case 51 is mounted to the camera channel port 23 and includes an inner peripheral surface formed with guide grooves 512 extending along an axial direction and a peripheral wall formed with a guide hole 513 extending in the axial direction. The slide member 52 is slidable with respect to the connector case 51 and includes a shaft part 521 and a guide part 523. The shaft part 521 extends inside the connector case 51 and a part of the shaft part 521 protrudes to the proximal end side of the connector case 51. A male screw part 522 is formed in a proximal end portion of the shaft part 521 and the cable tube 35 of the camera 30 is adhesively fixed to the inside of the shaft part 521 in a state of being inserted through the shaft part 521. The guide part 523 is formed integrally with the shaft part 521 so as to surround a distal end portion of the shaft part 521 and includes an outer peripheral surface formed with ridge parts 524 to be guided by the guide grooves 512 of the connector case 51 and an outer peripheral side formed with a protrusion part 525 to be guided by the guide hole 513. The rotation knob 53 is positioned on a proximal end side of the connector case 51, is restricted from moving in the axial direction, and includes a female screw part 531 that is screwed into the male screw part 522 of the shaft part 521 of the slide member 52. When the rotation knob 53 is rotated in one direction, the camera position adjustment mechanism slides the slide member 52 from the proximal end position to the distal end position so that the distal end of the camera 30 is moves from the first position (the distal end position of the camera 30 illustrated in FIG. 5A) to the second position (the distal end position of the camera 30 illustrated in FIG. 5B), and when the rotation knob 53 is rotated in the other direction, the camera position adjustment mechanism slides the slide member 52 from the distal end position to the proximal end position so that the distal end of the camera 30 is moves from the second position to the first position.

Figure 4A:
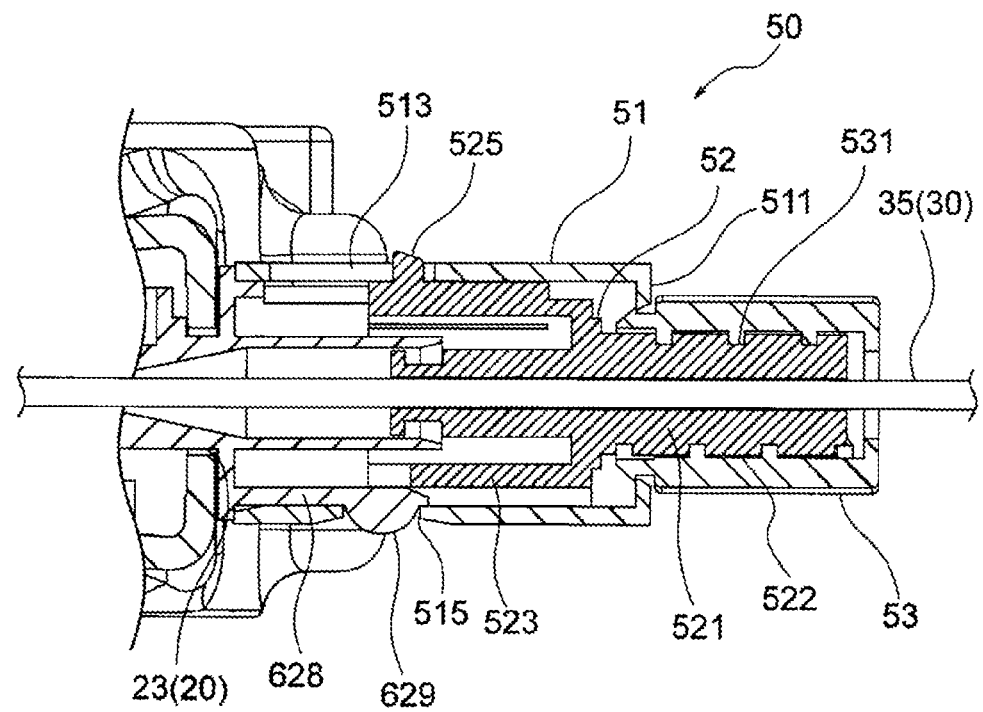
FIG. 4A is a cross-sectional view illustrating a state where a slide member of a camera connector constituting the endoscope illustrated in FIG. 1 is in a proximal end position.
Figure 4B:
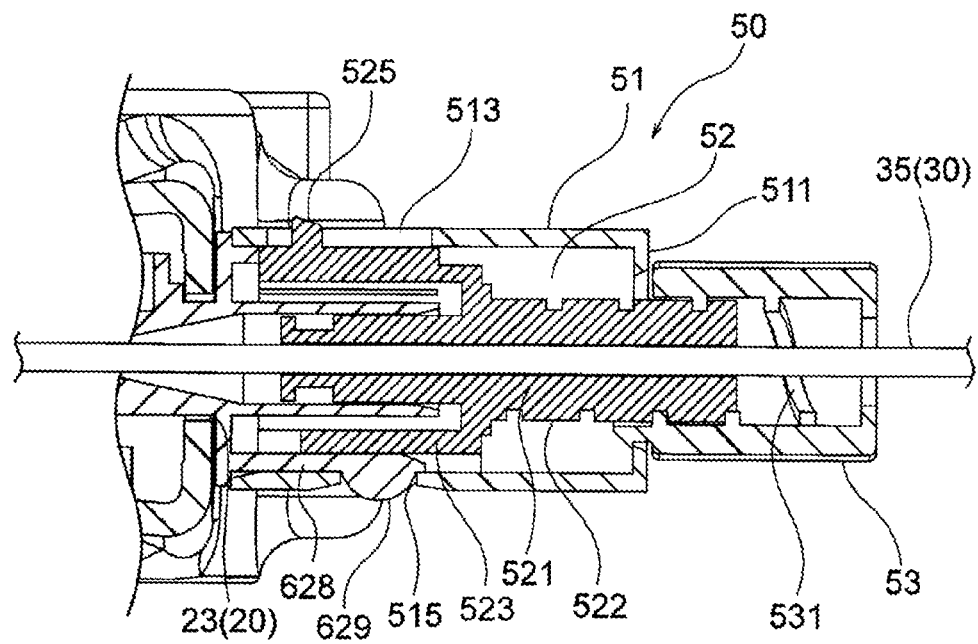
FIG. 4B is a cross-sectional view illustrating a state where the slide member of the camera connector constituting the endoscope illustrated in FIG. 1 is in a distal end position.
Figure 5A:
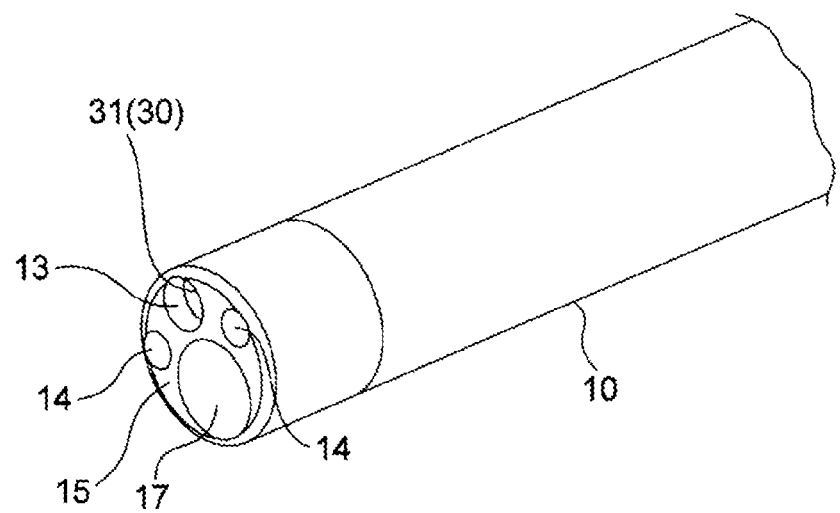
FIG. 5A is a perspective view illustrating a state where a distal end of the camera constituting the endoscope illustrated in FIG. 1 is located at a first position on a proximal end side of a distal end surface of a shaft.
Figure 5B:
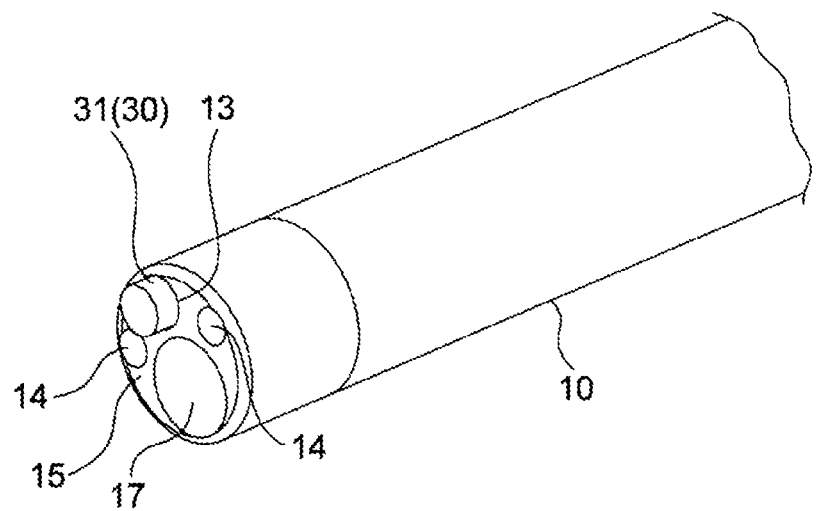
FIG. 5B is a perspective view illustrating a state where the distal end of the camera constituting the endoscope illustrated in FIG. 1 is located at a second position on a distal end side of the distal end surface of the shaft.
Figure 6:
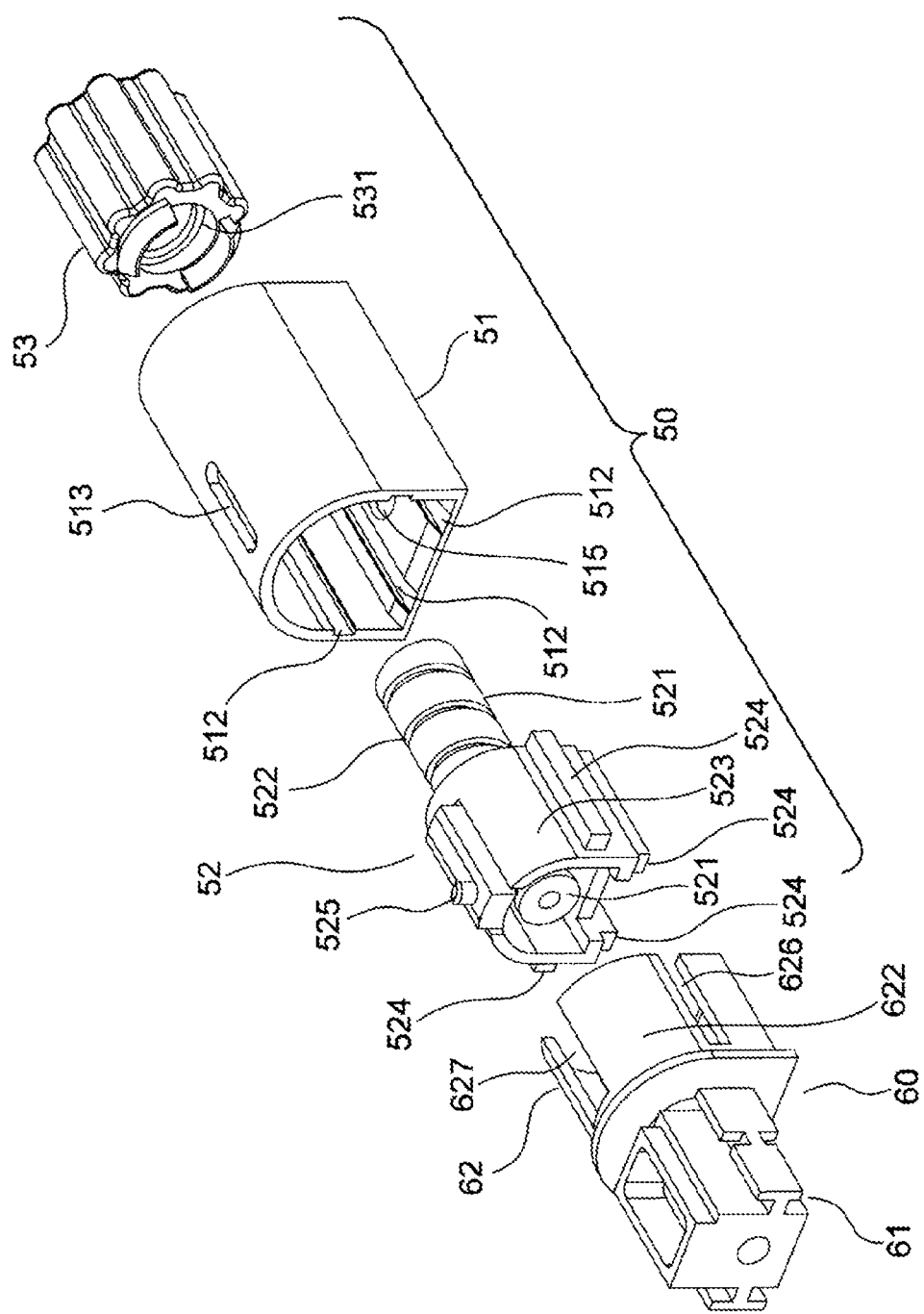
FIG. 6 is a perspective view illustrating in an exploded manner constitution components of a camera position adjustment mechanism and a connector mounting restriction mechanism in the endoscope illustrated in FIG. 1.
Figure 7:
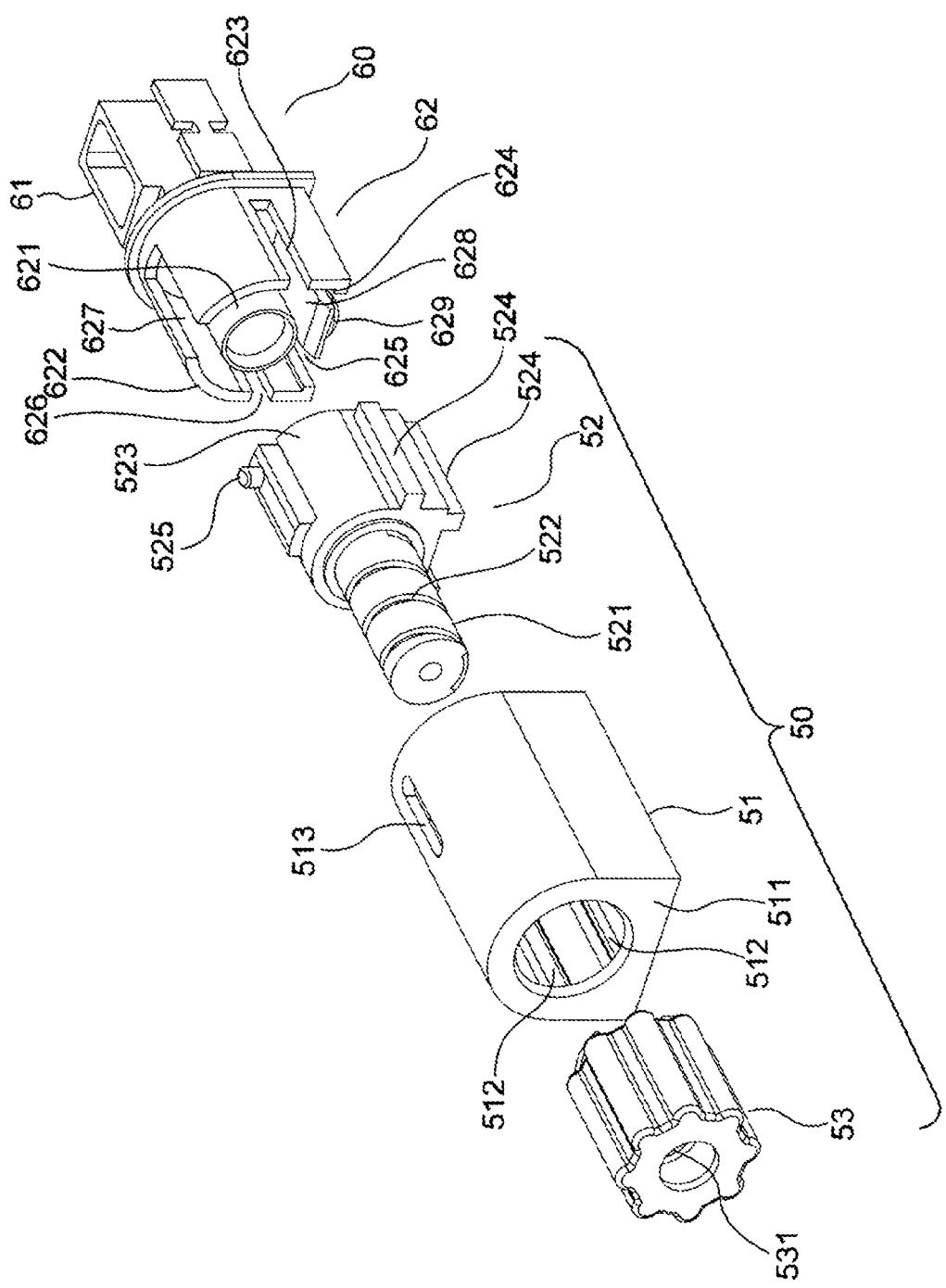
FIG. 7 is a perspective view illustrating in an exploded manner the constitution components of the camera position adjustment mechanism and the connector mounting restriction mechanism in the endoscope illustrated in FIG. 1.

Here, the "proximal end position" is a position where the slide member 52 cannot further move to the proximal end side, as illustrated in FIG. 4A, and the "distal end position" is a position where the slide member 52 cannot further move to the distal end side, as illustrated in FIG. 4B.

The camera position adjustment mechanism includes the connector case 51, the slide member 52, and the rotation knob 53.

The connector case 51 is a constituent member of the camera connector 50 mounted to the camera channel port 23 via a port-side connector described later, and is formed of a tubular body including an arch-shaped portion.

The guide grooves 512 extending along the axial direction are formed on the inner peripheral surface of the connector case 51, and the guide hole 513 extending along the axial direction is formed in a peripheral wall of the arch-shaped portion.

The slide member 52 includes the shaft part 521 and the guide part 523 integrally formed with the shaft part 521 so as to surround the distal end portion of the shaft part 521.

The shaft part 521 of the slide member 52 extends inside the connector case 51, and a part of the shaft part 521 protrudes from an opening formed in a proximal end surface 511 of the connector case 51 to the proximal end side.

The male screw part 522 is formed in the proximal end portion of the shaft part 521.

As illustrated in FIGS. 4A and 4B, the cable tube 35 of the camera 30 is adhesively fixed to the inside of the shaft part 521 in a state of being inserted through the shaft part 521.

The guide part 523 of the slide member 52 includes an arch-shaped portion corresponding to the shape of the connector case 51, and is integrally formed with the shaft part 521 so as to surround the distal end portion of the shaft part 521.

The ridge parts 524 to be guided by the guide grooves 512 of the connector case 51 are formed on an outer peripheral surface of the guide part 523.

Furthermore, the protrusion part 525 to be guided by the guide hole 513 of the connector case 51 is formed on an outer peripheral side of the arch-shaped portion of the guide part 523.

The rotation knob 53 is arranged on the proximal end side of the connector case 51.

The female screw part 531 to be screwed into the male screw part 522 of the shaft part 521 of the slide member 52 is formed on an inner peripheral side of the rotation knob 53.

The rotation knob 53 is restricted from moving in the axial direction with respect to the connector case 51, and when the rotation knob 53 is rotated, the slide member 52 slides with respect to the connector case 51.

Furthermore, when the rotation knob 53 is rotated to slide the slide member 52, the cable tube 35 that is adhesively fixed in the shaft part 521 also moves in the axial direction with respect to the connector case 51.

According to the camera position adjustment mechanism having the configuration described above, when the rotation knob 53 is rotated in one direction to slide the slide member 52 from the proximal end position (the position illustrated in FIG. 4A) to the distal end position (the position illustrated in FIG. 4B), it is possible to move the distal end of the camera 30 from the first position (the distal end position of the camera 30 illustrated in FIG. 5A) to the second position (the distal end position of the camera 30 illustrated in FIG. 5B), and when the rotation knob 53 is rotated in the other direction to slide the slide member 52 from the distal end position to the proximal end position, it is possible to move the distal end of the camera 30 from the second position to the first position.

In the camera position adjustment mechanism described above, in a case where the camera connector 50 is mounted to the camera channel port 23 in a state where the slide member 52 is not in the proximal end position, the distal end of the camera 30 may protrude from the opening of the camera channel 13 on the distal end surface 15 of the shaft 10.

If insertion of the shaft 10 into the body is performed in a state where the distal end of the camera 30 protrudes from the opening of the camera channel 13, the distal end of the camera 30 may damage tissue in the body, or may internally damage a channel of the delivery device (for example, a master endoscope such as a duodenum endoscope) for guiding the camera 30 (the camera head 31) into the vicinity of a target site, or the camera 30 may be damaged.

Thus, the endoscope 100 of the present embodiment includes a connector mounting restriction mechanism that prevents the camera connector 50 from being mounted to the camera channel port 23 when the slide member 52 is not in the proximal end position (when the distal end of the camera 30 may be protruding from the opening of the camera channel 13).

The connector mounting restriction mechanism includes a port-side connector 60 mounted to the camera channel port 23 so as to be interposed between the camera channel port 23 and the camera connector 50.

A distal end portion 61 of the port-side connector 60 is inserted into the handle 20 from the camera channel port 23.

A proximal end portion 62 of the port-side connector 60 includes an inner tube part 621 forming an insertion passage for the shaft part 521 of the slide member 52 (the cable tube 35 adhesively fixed in the shaft part 521), and an outer tube part 622 having an outer peripheral shape formed according to an inner peripheral shape of the connector case 51.

A peripheral wall of the outer tube part 622 is formed with notches 623 to 626 for avoiding, when the slide member 52 slides, contact with the ridge parts 524 formed in the guide part 523, and a notch 627 for avoiding, when the slide member 52 slides, contact with the protrusion part 525 formed in the guide part 523. Furthermore, a protrusion 629 having a hemispherical shape is formed on an outer peripheral side of a peripheral wall portion 628 that is sandwiched between the notches 624 and 625 so as to obtain flexibility.

On the other hand, a peripheral wall of the connector case 51 is formed with a through hole 515 having a circular shape into which the protrusion 629 is fitted when the proximal end portion 62 of the port-side connector 60 is inserted into the connector case 51.

Figure 8A:
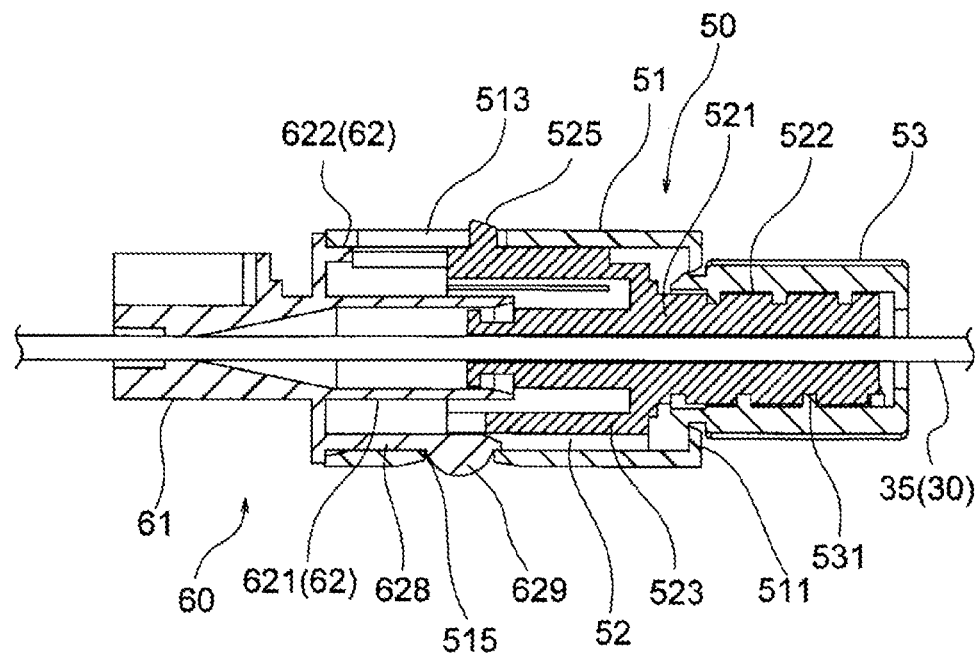
FIG. 8A is a cross-sectional view illustrating a state where a port-side connector and the camera connector constituting the endoscope illustrated in FIG. 1 are coupled.

According to the connector mounting restriction mechanism having such a configuration, when the slide member 52 is in the proximal end position and insertion of the proximal end portion 62 of the port-side connector 60 into the connector case 51 is performed to couple the port-side connector 60 and the camera connector 50, the peripheral wall portion 628 bends and the protrusion 629 retracts inward so that the protrusion 629 does not hinder the insertion of the port-side connector 60. Upon completion of the insertion of the proximal end portion 62 of the port-side connector 60 into the connector case 51, as illustrated in FIG. 8A, the bent peripheral wall portion 628 returns to the original posture, and the protrusion 629 is fitted into the through hole 515 of the connector case 51. As a result, the port-side connector 60 and the camera connector 50 are coupled, and the camera connector 50 is mounted to the camera channel port 23 via the port-side connector 60.

Figure 8B:
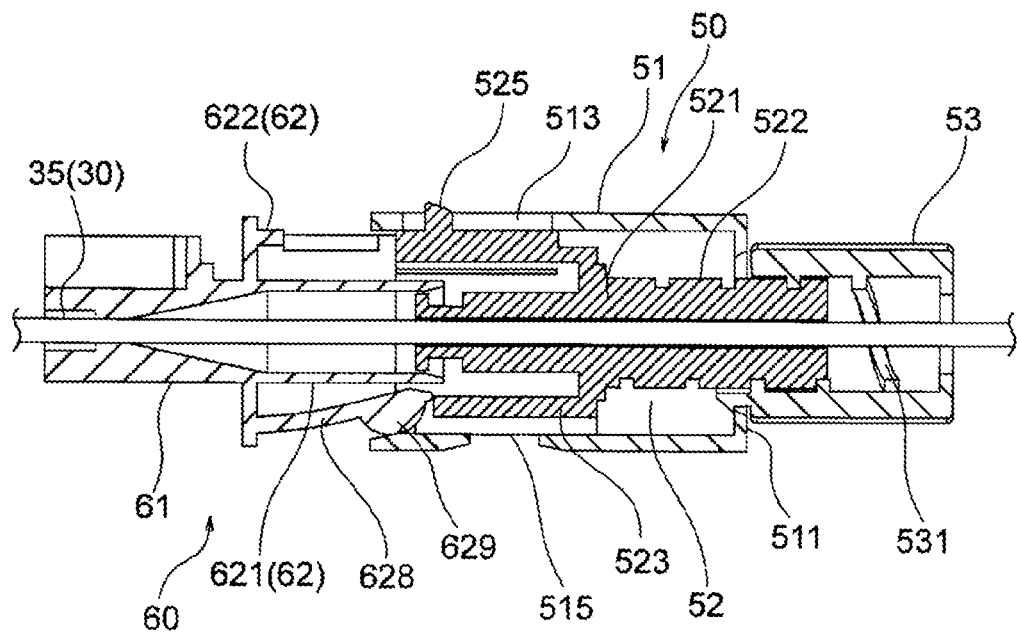
FIG. 8B is a cross-sectional view illustrating a state where the coupling between the port-side connector and the camera connector constituting the endoscope illustrated in FIG. 1 is restricted.
Figure 9:
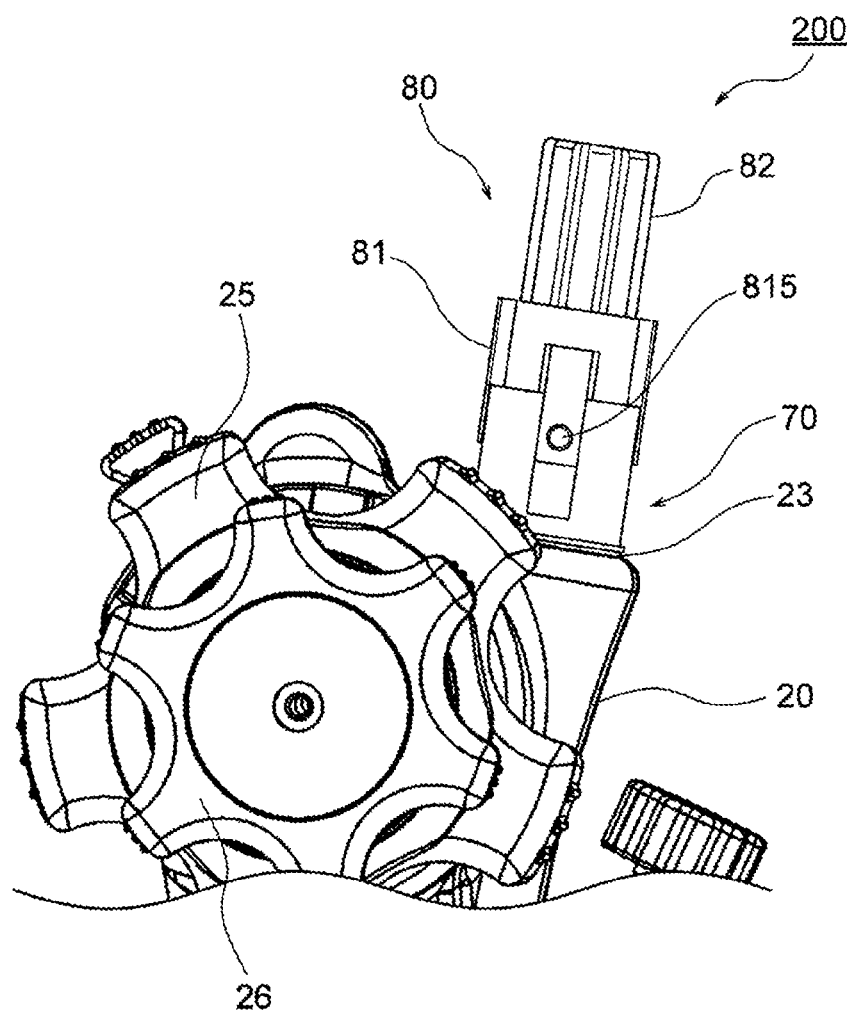
FIG. 9 is an explanatory diagram illustrating a main part of the outer appearance of a second embodiment of an endoscope of the present invention.

When the slide member 52 is not in the proximal end position and insertion of the proximal end portion 62 of the port-side connector 60 into the connector case 51 is performed, as illustrated in FIG. 8B, the distal end of the slide member 52 interferes with the peripheral wall portion 628 in the inwardly bent state so that it is not possible to insert the port-side connector 60, and therefore, the camera connector 50 cannot be coupled to the port-side connector 60, and the camera connector 50 cannot be mounted to the camera channel port 23.

According to the endoscope 100 of the present embodiment, after being used, the camera 30 including an expensive solid-state image sensor can be separated from the handle and the shaft and cleaned, making it possible to incorporate and reuse the camera 30 as a constituent component of the endoscope 100.

Furthermore, the camera position adjustment mechanism and the connector mounting restriction mechanism make it is possible to reliably prevent the shaft 10 from being inserted into the delivery device or the body when the camera 30 protrudes from the opening of the camera channel 13 in the distal end surface 15 of the shaft 10.

In addition, the camera position adjustment mechanism utilizing the feed screw to reciprocate the camera 30 makes it possible to precisely adjust the distal end position of the camera 30 with respect to the distal end surface 15 of the shaft 10.

Second Embodiment

An endoscope 200 of the present embodiment is similar to the first embodiment, except that a specific mechanism of the camera position adjustment mechanism for displacing the distal end of the camera 30 between the first position and the second position is different. Therefore, in the present embodiment illustrated in FIGS. 9 to 12, constitution elements that are the same as in the first embodiment are designated by the same correspondences as those in FIGS. 1 to 8 (FIGS. 8A and 8B), and description thereof will be omitted.

The camera position adjustment mechanism of the endoscope 200 according to the present embodiment includes a fixed member 70 mounted to the camera channel port 23, a movable member 80 configured to move in the axial direction with respect to the fixed member 70, and a structure (a click-producing projection part 729 and a click-producing indentation part 819) that is interposed between the fixed member 70 and the movable member 80 to provide a click feeling.

A distal end portion of the fixed member 70 constituting the camera position adjustment mechanism is inserted from the camera channel port 23 into the handle 20.

A proximal end portion of the fixed member 70 includes an inner tube part 71 forming an insertion passage of the cable tube 35, and an outer tube part 72 having a tubular shape and including an arch-shaped portion. Notches 723 to 727 are formed in a peripheral wall of the outer tube part 72. Furthermore, the click-producing projection part 729 is formed on an inner peripheral side of a peripheral wall portion 728 that is sandwiched between the notches 724 and 725 so as to obtain flexibility.

The movable member 80 constituting the camera position adjustment mechanism includes a distal end portion 81 having an outer peripheral shape formed according to an inner peripheral shape of the outer tube part 72 of the fixed member 70, and a proximal end portion 82 serving as an operation knob.

Figure 10A:
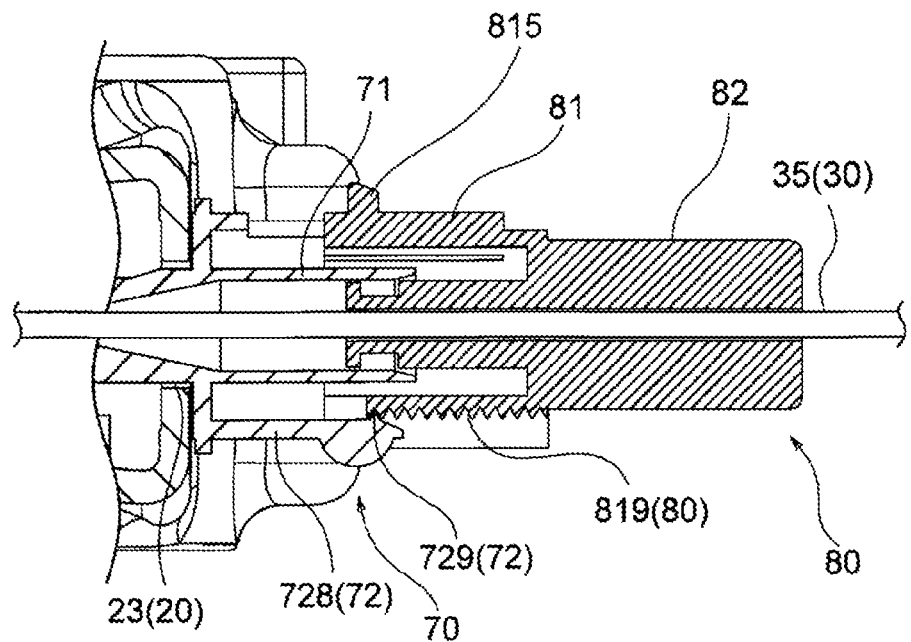
FIG. 10A is a cross-sectional view illustrating a state where a movable member constituting the endoscope illustrated in FIG. 9 is in a proximal end position.
Figure 10B:
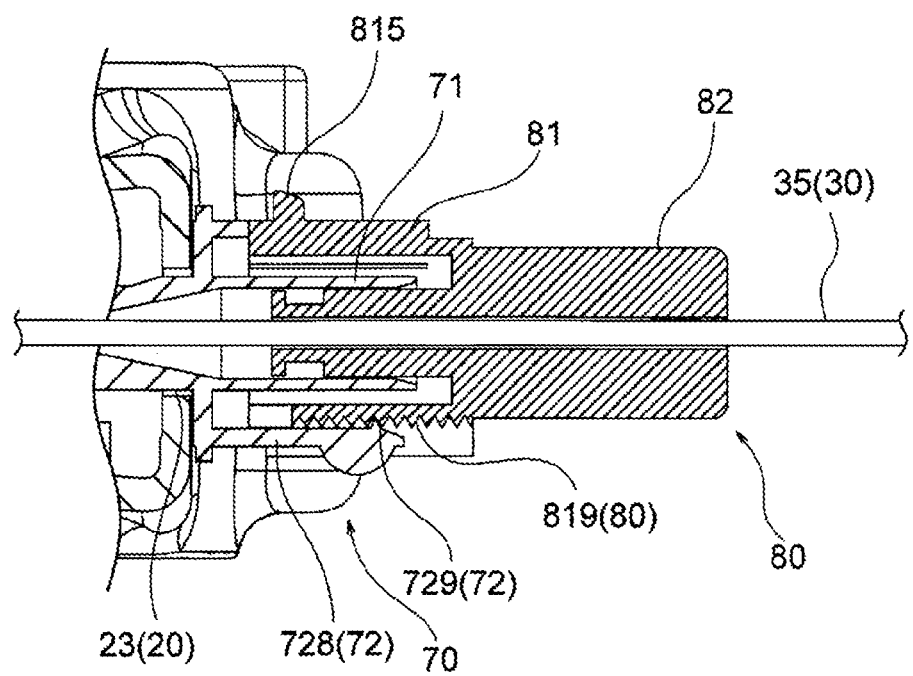
FIG. 10B is a cross-sectional view illustrating a state where the movable member constituting the endoscope illustrated in FIG. 9 is in a distal end position.
Figure 11:
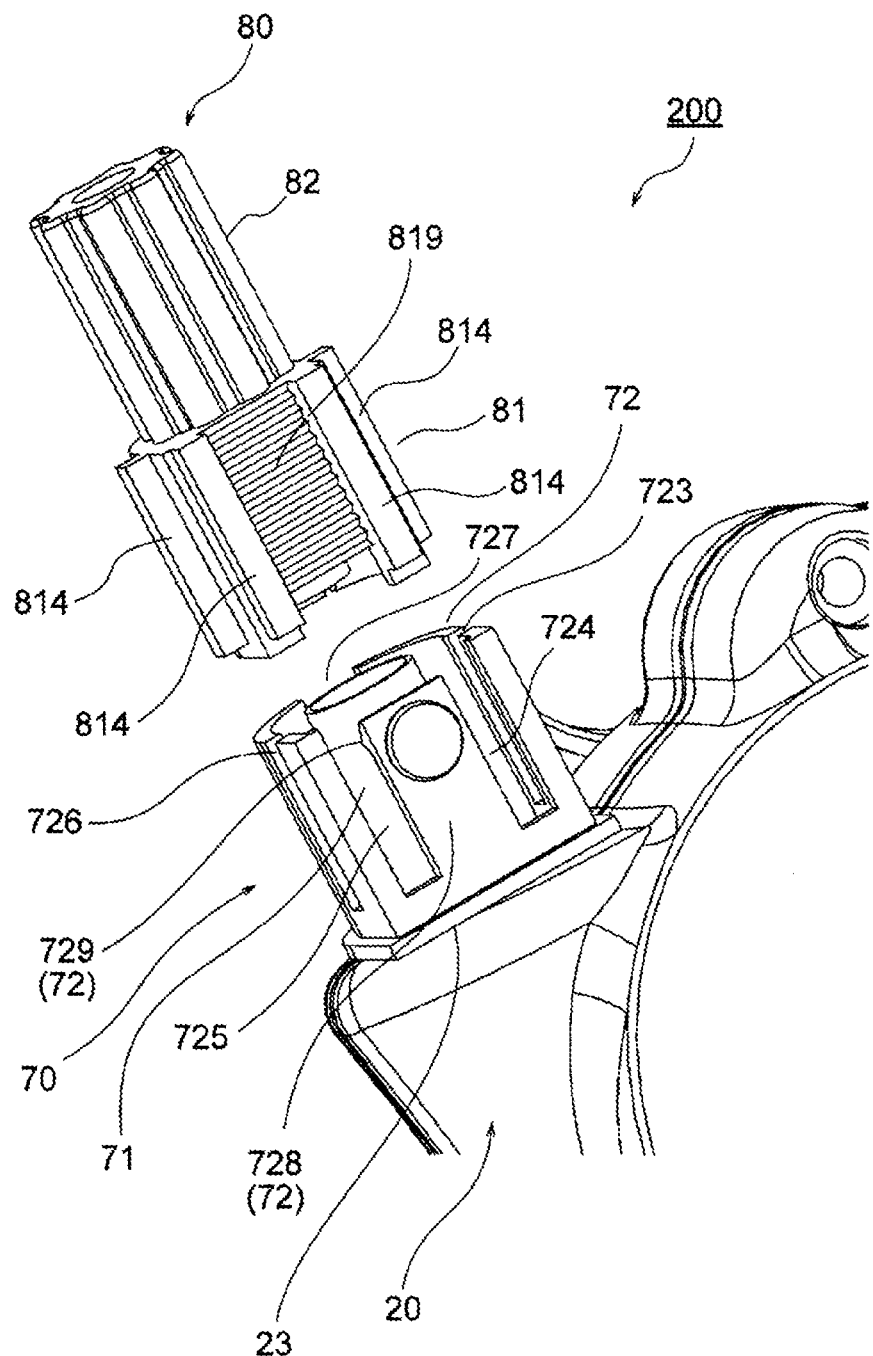
FIG. 11 is a perspective view illustrating a fixed member and the movable member constituting the endoscope illustrated in FIG. 9.
Figure 12:
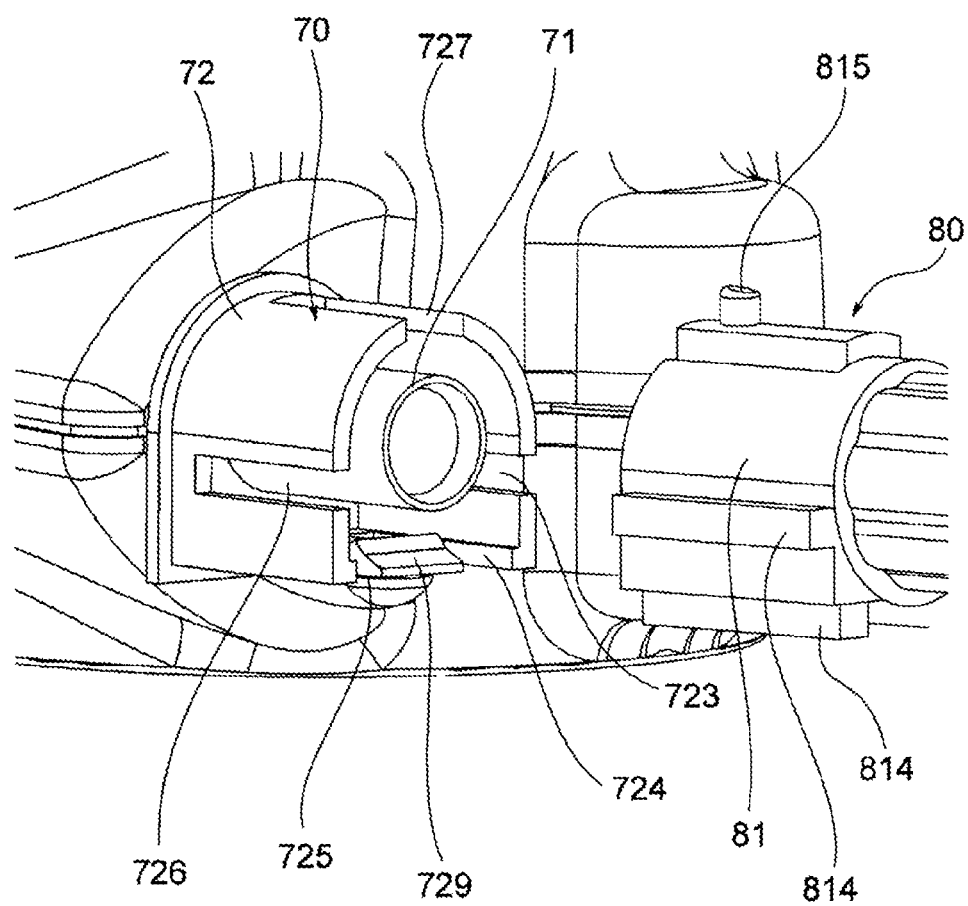
FIG. 12 is a perspective view illustrating the fixed member and the movable member constituting the endoscope illustrated in FIG. 9.

As illustrated in FIGS. 10A and 10B, the movable member 80 is formed with a through hole along a central axis of the movable member 80, and the cable tube 35 of the camera 30 is adhesively fixed to the movable member 80 in a state of being inserted through the through hole.

Ridge parts 814 to be guided by the notches 723 to 726 when the movable member 80 is inserted into the fixed member 70 are formed on an outer peripheral surface of the distal end portion 81 of the movable member 80, and a protrusion part 815 to be guided by the notch 727 is formed on an outer peripheral side of the distal end portion 81 of the movable member 80.

Furthermore, the click-producing indentation part 819 meshing with the click-producing projection part 729 is formed on the outer peripheral side of the distal end portion 81 of the movable member 80 facing the click-producing projection part 729 formed on the inner peripheral side of the peripheral wall portion 728 of the fixed member 70.

According to the camera position adjustment mechanism having such a configuration, when the movable member 80 in the proximal end position is pushed to be moved to the distal end position, the distal end of the camera 30 can be moved from the first position to the second position, and when the movable member 80 in the distal end position is retracted to be moved to the proximal end position, the distal end of the camera 30 can be moved from the second position to the first position. In addition, it is possible to provide a click feeling generated by the click-producing projection part 729 and the click-producing indentation part 819 in response to the movement of the movable member 80, so that the distal end position of the camera 30 can be precisely adjusted.

REFERENCE SIGNS LIST

100 Endoscope
10 Shaft
13 Camera channel
14 Water supply channel
15 Distal end surface of shaft
17 Forceps channel
20 Handle
21 Grip
23 Camera channel port
25, 26 Operation knob
27 Forceps channel port
30 Camera
31 Camera head
35 Cable tube
50 Camera connector
51 Connector case
511 Proximal end surface
512 Guide groove
513 Guide hole
515 Through hole
52 Slide member
521 Shaft part
522 Male screw part
523 Guide part
524 Ridge part
525 Protrusion part
53 Rotation knob
531 Female screw part
60 Port-side connector
61 Distal end portion
62 Proximal end portion
621 Inner tube part
622 Outer tube part
623 to 627 Notch
628 Peripheral wall portion
629 Protrusion having hemispherical shape
200 Endoscope
70 Fixed member
71 Inner tube part
72 Outer tube part
723 to 727 Notch
728 Peripheral wall portion
729 Click-producing projection part
80 Movable member
81 Distal end portion
814 Ridge part
815 Protrusion part
819 Click-producing indentation part
82 Proximal end portion (operation knob)

The invention claimed is:

1. An endoscope, comprising:
a shaft to be inserted into a body;
a handle mounted on a proximal end side of the shaft; and
a camera including a cable tube and a camera head, the camera head being equipped with an image sensor, wherein
the camera is separable from the handle and the shaft;
wherein the shaft is formed with a camera channel in which the camera is arranged,
the handle is provided with a camera channel port communicating with the camera channel, and
the cable tube of the camera is attached to a camera connector mounted to the camera channel port;
wherein the camera connector includes a camera position adjustment mechanism configured to reciprocate the camera to displace the camera between a first position where, when the camera connector is mounted to the camera channel port, a distal end of the camera arranged in the camera channel is located on a proximal end side of a distal end surface of the shaft where the camera channel opens, and a second position where, when the camera connector is mounted to the camera channel port, the distal end of the camera is located on a distal end side of the distal end surface of the shaft.

2. The endoscope according to claim 1, wherein a distance from the first position to the second position is from 2 to 100 mm.

3. The endoscope according to claim 1, wherein the camera position adjustment mechanism includes a connector case mounted to the camera channel port and having an inner peripheral surface formed with a guide groove extending along an axial direction,
a slide member slidable with respect to the connector case and including a shaft part and a guide part, the shaft part extending inside the connector case and a part of the shaft part protruding to a proximal end side of the connector case, a male screw part being formed at least in a proximal end portion of the shaft part, and the cable tube of the camera being fixed to an inside of the shaft part in a state of being inserted through the shaft part, the guide part being integrally formed with the shaft part and surrounding a distal end portion of the shaft part, the guide part having an outer peripheral surface formed with a ridge part to be guided by the guide groove, and a rotation knob positioned on the proximal end side of the connector case, restricted from moving in the axial direction, and including a female screw part to be screwed into the male screw part of the shaft part of the slide member.

4. The endoscope according to claim 3, further comprising a connector mounting restriction mechanism configured to prevent the camera connector from being mounted to the camera channel port when the slide member of the camera position adjustment mechanism is not in the proximal end position.

5. The endoscope according to claim 4, wherein the connector mounting restriction mechanism includes a port-side connector mounted to the camera channel port and interposed between the camera channel port and the camera connector, the port-side connector is formed with an insertion passage for the cable tube, when the slide member is in the proximal end position, a proximal end portion of the port-side connector is not prevented from being inserted into the connector case to couple the port-side connector and the camera connector, and when the slide member is not in the proximal end position and insertion of the proximal end portion of the port-side connector into the connector case is performed, the insertion of the proximal end portion of the port-side connector is prevented by interference between the proximal end portion of the port-side connector and a distal end of the slide member.

6. The endoscope according to claim 5, wherein a through hole having a circular shape is formed in a peripheral wall of the connector case, a distal end portion of the port-side connector is inserted into the handle from the camera channel port, the proximal end portion of the port-side connector includes an inner tube part forming an insertion passage of the shaft part of the slide member and an outer tube part having an outer peripheral shape formed in accordance with an inner peripheral shape of the connector case, a peripheral wall of the outer tube part is formed with notches configured to allow contact with the ridge part of the guide part to be avoided when the slide member slides, and a protrusion having a hemispherical shape is formed on an outer peripheral side of a peripheral wall portion sandwiched between the notches and having flexibility.

7. The endoscope according to claim 1, wherein the camera position adjustment mechanism includes a fixed member mounted to the camera channel port and a movable member configured to move in the axial direction with respect to the fixed member, the cable tube of the camera being fixed to an inside of the movable member in a state of being inserted through the movable member, the camera position adjustment mechanism provides a click feeling in response to a movement of the movable member.

8. The endoscope according to claim 7, wherein the camera position adjustment mechanism includes a click-producing indentation part formed in the movable member and a click-producing projection part provided in the fixed member and meshing with the click-producing indentation part.

9. The endoscope according to claim 1, wherein the camera is equipped with an optical fiber.

10. The endoscope according to claim 1, wherein an outer diameter of the shaft is from 1.1 to 7.0 mm and a diameter of the camera channel is from 0.7 to 3.0 mm, and the shaft is formed with a forceps channel having a diameter from 0.3 to 3.0 mm.

* * * * *